United States Patent
Johnson et al.

(10) Patent No.: US 7,809,816 B2
(45) Date of Patent: Oct. 5, 2010

(54) IMAGING VIEWER SYSTEMS AND METHODS

(75) Inventors: Brett D. Johnson, Acworth, GA (US); Laurence Siegel, Atlanta, GA (US); Marty Smith, Atlanta, GA (US); Adrian Popescu, Marietta, GA (US); Charles Frederick Hart, Atlanta, GA (US); Larry Kent, Jr., Loganville, GA (US)

(73) Assignee: AT&T Intellectual Property I, L.P., Reno, NV (US)

( * ) Notice: Subject to any disclaimer, the term of this patent is extended or adjusted under 35 U.S.C. 154(b) by 386 days.

(21) Appl. No.: 11/523,466

(22) Filed: Sep. 19, 2006

(65) Prior Publication Data

US 2008/0071895 A1 Mar. 20, 2008

(51) Int. Cl.
*G06F 15/173* (2006.01)
*G06F 15/16* (2006.01)
*G06F 13/42* (2006.01)
*G06F 11/00* (2006.01)

(52) U.S. Cl. .............. 709/223; 709/224; 709/208; 340/825; 370/252; 714/39

(58) Field of Classification Search .............. None
See application file for complete search history.

(56) References Cited

U.S. PATENT DOCUMENTS

| | | | |
|---|---|---|---|
| 5,987,510 A * | 11/1999 | Imai et al. ................ 709/219 |
| 6,876,759 B2 | 4/2005 | Keller et al. |
| 6,934,698 B2 | 8/2005 | Judd et al. |
| 6,938,211 B1 | 8/2005 | Chang et al. |
| 7,028,182 B1 | 4/2006 | Killcommons |
| 2001/0041991 A1 | 11/2001 | Segal et al. |
| 2002/0103935 A1* | 8/2002 | Fishman et al. .......... 709/246 |
| 2002/0128873 A1* | 9/2002 | Shimizu et al. .............. 705/3 |
| 2004/0114172 A1* | 6/2004 | Ohyama et al. .......... 358/1.13 |
| 2004/0257608 A1* | 12/2004 | Tipirneni ................. 358/1.15 |
| 2005/0148849 A1* | 7/2005 | Heere et al. ............... 600/407 |
| 2006/0036625 A1 | 2/2006 | Judd et al. |
| 2006/0058603 A1* | 3/2006 | Dave et al. ............... 600/407 |
| 2006/0218482 A1* | 9/2006 | Ralston et al. .......... 715/500.1 |
| 2007/0239616 A1* | 10/2007 | Walline et al. ............. 705/59 |
| 2009/0086701 A1* | 4/2009 | Lohmar et al. ........... 370/345 |

* cited by examiner

*Primary Examiner*—Ario Etienne
*Assistant Examiner*—Ho Shiu
(74) *Attorney, Agent, or Firm*—Scott P. Zimmerman PLLC

(57) ABSTRACT

Systems and methods according to the present invention address this need and others by providing images to a remote user through the use of instant messaging techniques.

24 Claims, 2 Drawing Sheets

IMAGING VIEWER SYSTEMS AND METHODS

BACKGROUND

The ability to review data-intensive images is a useful tool, e.g., in the medical profession. Many of the issues involving patient health can only be seen or verified by some of the imaging techniques that exist today and cannot be reliably diagnosed by an external exam alone. For example, if a patient's symptoms led a physician to believe that the patient had a cracked rib an x-ray of the area could be used to verify the physician's belief. Often, for many types of medical images, a patient would go to a location remote from the physician's office and have an image taken.

As technology develops, improvements to communication systems and computers have created the ability to transfer large amounts of data relatively quickly over large distances. At the same time, the types of medical images and the amount of data these images contain has continued to grow. Some of the types of medical images currently used by physicians for patient diagnostics include: x-ray, magnetic resonance imaging (MRI), computed tomography (CT), electrocardiogram (ECG), ultrasonography, nuclear medicine and digitized radiography. A standard format for medical images is the Digital Imaging Communications in Medicine (DICOM) format. This format allows a common image format to be used among a multitude of different imaging equipment.

With the advances in medical science, more options for medical imagery now exist that a physician can use to assist in patient diagnostics. Sometimes people are sent to multiple locations in order to have different types of images taken. The image would be taken, processed at the location, and then a report would be generated. The report would get back to the physician days later through one or more of a number of different channels such as: the patient returning to the imaging location(s) to pick-up and deliver the image film(s) and report(s) to their physician or the imaging location specialist mailing the report and/or film(s) to the physician. These methods are slow and inefficient.

Teleradiology (which term refers generally to the transmission of digitized medical images) improved upon these purely manual delivery methods in part, by allowing many types of image taking devices to send their images to a central processing station. For example, as shown in FIG. 1, a patient is referred by a physician to imaging center 102. Depending upon the imaging requested, the patient could get an x-ray taken in x-ray imaging room 104, a magnetic resonance image (MRI) taken in MRI room 106 and an ultrasound in ultrasound room 108. These medical images are then forwarded electronically to the film processing lab 110 for processing. Upon completion of this process, the image films and any associated information either needs to be picked up and hand carried or mailed to a physician's office 112. Thus teleradiology techniques initially allowed a patient to get all of the imaging needed performed in one location, as well as getting the reports generated at one location, but did not improve the steps involved with image report delivery to the patient's physician.

A next logical step in the usage of medical images is to allow remote access to images and their associated reports for physicians and/or patients. Some of the advantages associated with such an improvement would be a faster turn around time on diagnosing patient problems and cost reductions. Some challenges associated with this step of allowing remote access are privacy/security concerns, format of the medical image, quality of the image, notification and ensuring that the remote station had the correct capabilities to view the image (s).

In conjunction with remote medical image viewing, notification to the physician and/or patient that report delivery occurred is also desirable. One method of notification has been described in U.S. Pat. No. 6,934,698 B2 filed on Dec. 20, 2000, entitled "Medical Image Management System" and which is hereafter referred to as the "698 application". In the 698 application, upon completion of the computations related to the image, an email notification is sent to the person submitting the request or via a text message to a physician's pager. However, some limitations still exist when using the systems or methods described in this patent. For example, if the physician was not close to his computer he could not view the images immediately. Moreover, there is limited to no ability to interact with the sender of the notification to query the status of other requests. Additionally, the difficulties associated with remotely viewing medical images also arise in other fields, e.g., geology, astronomy, and aerial imaging in which data-intensive images are recorded and analyzed.

Accordingly, there is a need for more efficient systems and methods for both viewing data-intensive images at remote locations and supplying notification of the readiness of such images for viewing to the relevant individuals.

SUMMARY

Systems and methods according to exemplary embodiments address this need and others by providing techniques for processing medical images and their associated notifications.

According to one exemplary embodiment, a device for processing images comprising: a server for receiving a notification indicating that an image is available for transmission to the device from a remote location, transmitting a request for the image, and receiving the image; and a display for displaying the image and the notification.

According to another exemplary embodiment, a method for processing an image comprising the steps of: receiving a notification which indicates that an image is available for transmission from a remote location; transmitting a request for the image; and receiving the image for display.

According to another exemplary embodiment, a computer-readable medium containing instructions which, when executed on a computer, perform the steps of: receiving a notification which indicates that an image is available for transmission from a remote location; transmitting a request for the image; and receiving the image for display.

According to another exemplary embodiment, a system for processing medical images comprising: a first server in communication with a database, wherein the database contains medical images, a second server in communication with the first server, wherein the second server contains protocols for transmitting the medical images and the second server contains protocols for sending notifications, and an electronic device in communication with the second server, the electronic device comprising: a processor, wherein the processor receives and processes the images and the notifications, and a display for displaying the images and the notifications.

BRIEF DESCRIPTION OF THE DRAWINGS

The accompanying drawings illustrate exemplary embodiments of the present invention, wherein.

DETAILED DESCRIPTION

The following detailed description refers to the accompanying drawings. The same reference numbers in different drawings identify the same or similar elements. Also, the following detailed description does not limit the invention. Instead, the scope of the invention is defined by the appended claims.

Figure 1:
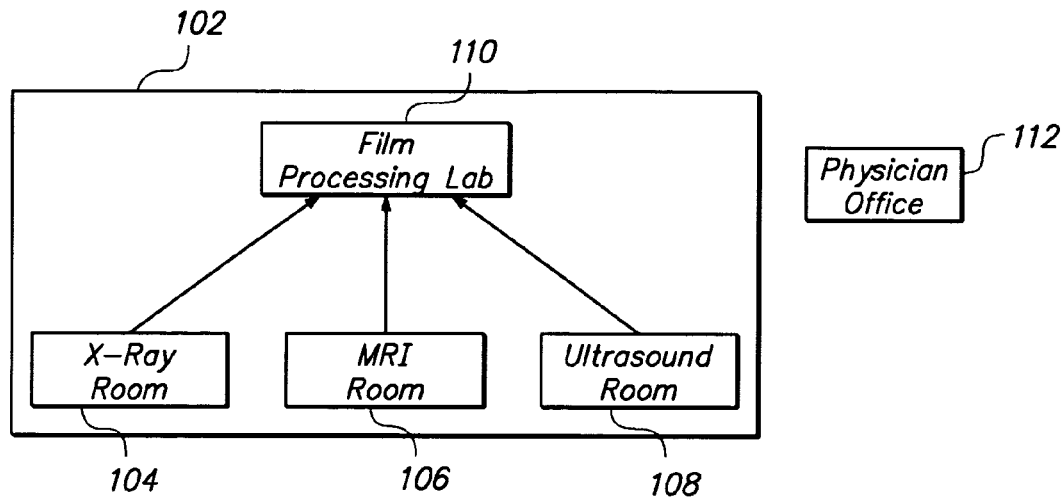
FIG. 1 depicts the conventional method for processing medical images to be received by a physician.
Figure 2:
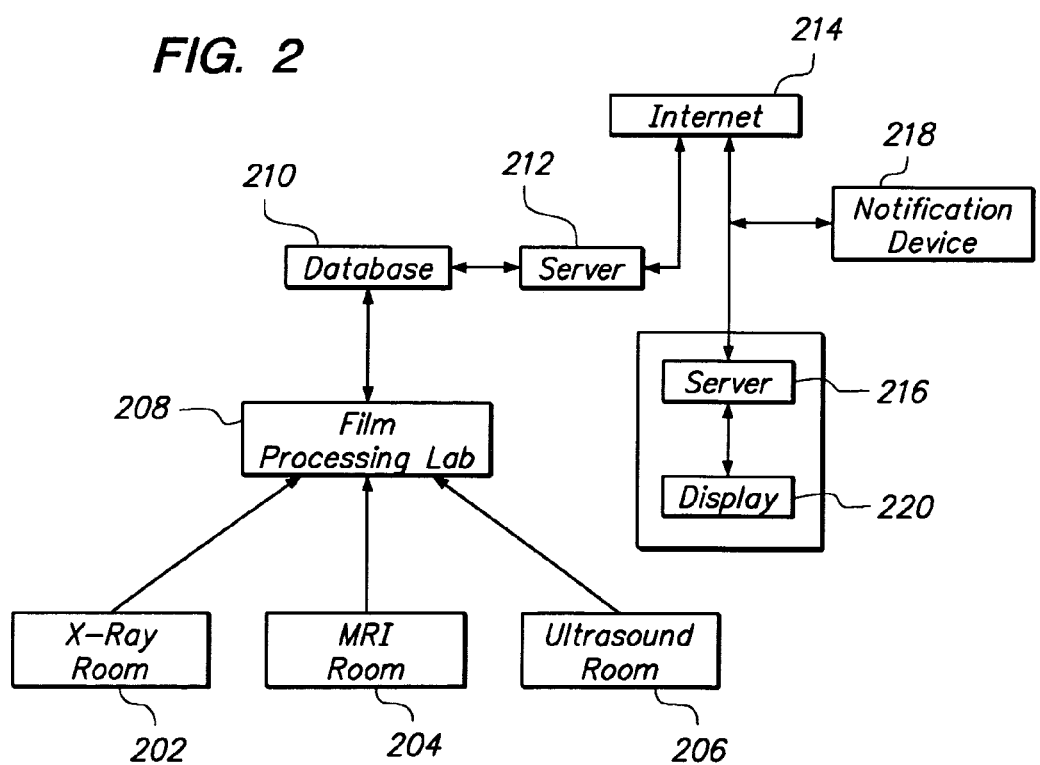
FIG. 2 depicts a system for processing and transmitting images according to an exemplary embodiment.

In order to provide some context for this description, an exemplary environment in which exemplary embodiments can be employed will now be described with respect to FIG. 2. The description that follows focuses on medical images for ease of illustration. It should be appreciated, however, that the invention is also applicable to other types of data-intensive images, e.g., geological images, astronomical images, satellite images, etc. Using medical images as an example, in one embodiment a patient can have a variety of medical images taken in different locations or labs, referred to herein as "rooms", such as, x-rays in x-ray room 202, MRIs in MRI room 204 and ultrasounds in ultrasound room 206. Those skilled in the art will appreciate that the present invention is equally applicable to other types of medical images, e.g., computed tomography, electrocardiogram, nuclear medicine images, digitized radiography, etc., and that the examples depicted in FIG. 2 are shown for illustrative purposes. The images taken in these rooms may be transmitted to a central location such as, film processing lab 208, for processing. When the images are received in film processing lab 208, pertinent information such as patient name, physician name and/or type of image are entered into the system and transmitted to database 210. This allows the server 212 to create a list or database of images indexed based on patients and/or physician of images that are being processed. Alternatively, other identification methods could be used. The images can be processed into physical films for pickup or distribution, or processed into a transmittable and viewable electronic format, such as DICOM and/or joint photographics expert group (JPEG). Additionally, a local technician may write up a report with his or her evaluation of the images. Like the images themselves, these reports can also be rendered in electronic form for transmission and subsequent viewage by, e.g., a physician and/or patient, as described below.

As an alternative to the transmission of images to the film processing lab, images may be digitally recorded and processed in each of the rooms 202-206. In yet another embodiment, different kinds of images may be recorded and stored in one or more digital imaging/processing device(s) 207. In either scenario, the digitally recorded images may be processed and the report generated in the device 207 and delivered directly to the database 210.

Upon completion of the image processing and the report write up, the processed images and report are relocated to a database 210. According to an exemplary embodiment, the DICOM images are stored in a photosharing section of database 210, while the JPEG images are stored in a filesharing section of database. Upon sending the images from the film processing lab 208 to the database 210, a notification signal is sent to server 212 by database 210. The server 212 then processes the notification message, matches it to information stored in database 210 and retrieves contact information for the relevant physician(s) (and/or patient). Notification of a viewable image is then sent from server 212 through a network, such as the Internet 214, to another server 216 and a notification device 218 (multiple notification devices (not shown) could be used based on user preferences). While the Internet 214 is shown as an example of a network useful for notifications, it should be appreciated that any other suitable network may be used.

Upon receipt of the notification, the user has the ability to view the image on the notification device 218 or upon display 220. In some cases, notification device 218 might only be capable of viewing the image a particular format, such as the JPEG format, so the user has the option of using display 220 (e.g., part of a personal computer in the physician's office or hospital) which is in communication with server 216 to view the higher quality image (DICOM image in this example) if desired. Additionally, there may be two-way communications between server 212 and both notification device 218 and server 216, which allow the user to query server 212 to determine the status of images to be viewed as will be described in more detail below.

Figure 3:
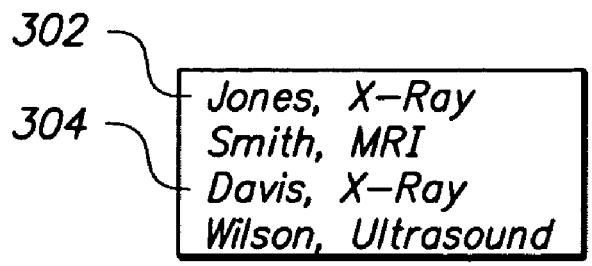
FIG. 3 illustrates a method to distinguish between processed and unprocessed images according to an exemplary embodiment.

Notification devices according to exemplary embodiments can be any electronic device capable of both receiving notification messages from a server and then being able to also view the referenced image in at least one of the image formats in which the medical image is stored in database 210. For example a notification device could be a laptop computer, a desktop computer, a personal digital assistant (PDA), a cell phone capable of receiving and displaying digital images, such as JPEG images, or any other electronic device capable of receiving and displaying the desired images. According to one exemplary embodiment, the notification message allows the user to see which image is currently ready for viewing as well as other images in the queue. For example, if a physician had two patients that had undergone both x-rays and MRIs, the physician could use her or his notification device to determine the status of the images. Then, the images ready for viewing could be listed on a display of the notification device 218 in a manner which is visually distinguishable from those images that were still being processed as shown in FIG. 3. In FIG. 3, images ready for viewing are displayed in capital letters 302, and images still being processed are displayed in lower case letters 304.

Additional or alternative visual techniques could be used to differentiate viewable images from images that are still being processed, such as black lettering for viewable images and grayed out lettering for images that are still being processed. The manner in which the notification device 218 is updated can vary as well. For example, according to one exemplary embodiment, the server 212 can "push" status updates to the notification device 218 as new images become available for viewing. Alternatively, the notification device 218 can query the server 212 when the user actuates an update command. Similarly, instead of a three-step process, i.e., notification, request, image delivery, the notification message could contain the medical image and/or report itself so that the physician could immediately view the image without first requesting it from server 212.

Figure 4:
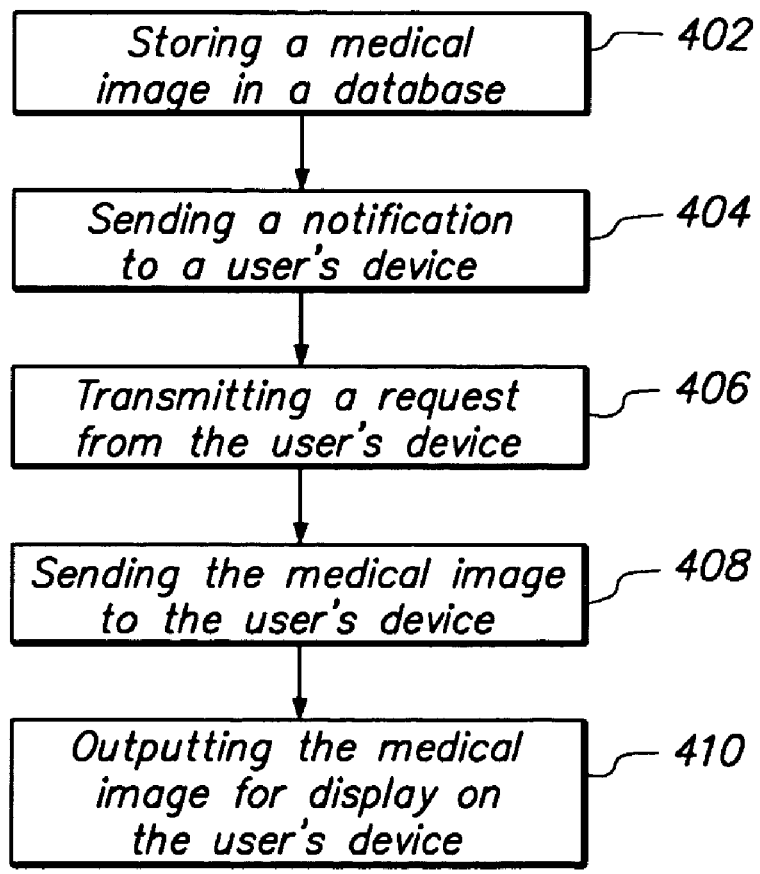
FIG. 4 shows a flowchart illustrating a method for transmitting images according to an exemplary embodiment.

According to another exemplary embodiment, a method for processing an image is illustrated in the flowchart of FIG. 4. Again, for illustrative purposes, the images described with reference to FIG. 4 are medical images. The first activity is storing a medical image in a database at step 402. The medical image can be one of image types listed above or any medical image that would benefit from these techniques. Next, a notification is sent to a user's device in step 404. This notification could be as described above or come in alternate forms, such as sound or voice. This is followed by transmitting a request from the user's device in step 406. This request may be, for example, a request for the processed image to be sent to the user's device. For those embodiments in which the image(s) are attached to the notification, the request could also be a status update on other images. Additionally, the user could direct the image to be sent to a different device than is currently being used. Next, the medical image is sent to the user's device in step 408. Lastly the medical image is output for display on the user's device in step 410.

According to one exemplary embodiment, notification messages are sent out through instant messaging. Referring back to FIG. 2, the notification messages may be sent from server 212. Server 212 may be a type of server that supports instant messaging to notification device 218 and/or server 216. For example, server 212 could be a Jabber server that uses a messaging and presence protocol, such as the Extensible Messaging and Presence Protocol (XMPP), which supports instant messaging. Additionally, a publish and subscribe (pub/sub) system that utilizes persistent or future searching could be combined with the instant messaging setup to send out notification messages when images are ready for transmittal to a user. Another issue of concern during the transmission of images is security. According to an exemplary embodiment, the images are kept in a secure database, accessed by only authorized personnel and transmitted in a secure fashion.

According to another exemplary embodiment, images can be displayed and manipulated on an electronic device that is also used as the notification device 218. For example, after a notification message has been received by a notification device 218 (in this example, a cell phone), the user sends back the request to server 212 to have the image sent to her or his cell phone. The cell phone receives the image and the user, e.g., the physician, decides to manipulate the image, e.g., to see features of the medical image which are significant to diagnose the patient. Exemplary image manipulation options may be to use various buttons to perform functions such as zooming, panning or rotating the image in order to better view the area of interest to assist in quick and timely patient diagnosis.

According to yet another exemplary embodiment, the server 212 knows the capabilities of the notification device 218, e.g., by retrieving pre-stored capabilities data from the database 210 indexed, e.g., by physician. Alternatively, for those embodiments where a request message is explicitly transmitted by the user of the notification device 218, the request message can include device capabilities information therein. In either event, the server 212 knows what format notification device 218 is capable of receiving images in, e.g., both DICOM and JPEG images or just JPEG images, and transmits the requested image(s) in those format(s) which the requesting device is capable of handling.

The above-described exemplary embodiments are intended to be illustrative in all respects, rather than restrictive, of the present invention. Thus the present invention is capable of many variations in detailed implementation that can be derived from the description contained herein by a person skilled in the art. All such variations and modifications are considered to be within the scope and spirit of the present invention as defined by the following claims. No element, act, or instruction used in the description of the present application should be construed as critical or essential to the invention unless explicitly described as such. Also, as used herein, the article "a" is intended to include one or more items.

What is claimed is:

1. A system for processing medical images comprising:
a processor executing code stored in memory that causes the processor to:
receive a notification indicating that a processed medical image is available for transmission from a remote location and indicating unprocessed medical images in a queue that have yet to be processed for display;
receive a user input to retrieve the processed medical image;
transmit a request for the processed medical image after receipt of the notification;
receive the processed medical image;
store the processed medical image in the memory;
create a list of medical images stored in the memory;
index the list of medical images based on a patient's name and on a physician's name;
store in a photosharing section of the memory any Digital Imaging Communications in Medicine (DICOM) formatted medical images;
store in a filesharing section of the memory any JPEG formatted medical images;
cause display of the processed medical image and the notification; and
visually distinguish the processed medical image in the notification from the unprocessed medical images in the queue that are yet to be processed.

2. The system of claim 1, wherein the code further causes the processor to receive an instant message as the notification.

3. The system of claim 1, wherein the medical image includes at least one of X-ray, magnetic resonance imaging, computed tomography, electrocardiogram, ultrasonography, nuclear medicine, or radiography in digital or analog form.

4. The system of claim 1, wherein the code further causes the processor to receive a version of the medical image based upon capabilities of a display.

5. The system of claim 1, wherein the code further causes the processor to create a list of medical images in a queue that are associated with the physician and that are available and unavailable for download.

6. The system of claim 5, wherein the code further causes the processor to store Digital Imaging Communications in Medicine (DICOM) formatted images in a photosharing section of the memory.

7. The system of claim 5, wherein the code further causes the processor to distinguish images in the list from unprocessed images not ready for display.

8. The system of claim 1, wherein the code further causes the processor to securely receive the medical image.

9. The system of claim 1, wherein the notification is at least one of visual, audible or vibrational.

10. The system of claim 1, wherein the system comprises at least one of a PC, PDA, cellphone or TV.

11. The system of claim 1, wherein the code further causes the processor to manipulate the medical image by performing at least one of zooming, panning or rotation.

12. A method for processing an image comprising:
receiving a notification at a processor, the notification indicating that a processed medical image is available for transmission from a remote location and indicating unprocessed medical images in a queue that have yet to be processed for display;
receiving a user input to retrieve the processed medical image;
transmitting a request for the processed medical image after receipt of the notification;
receiving the processed medical image;

storing the processed medical image in memory;
creating a list of medical images stored in the memory;
indexing the list of medical images based on a patient's name and on a physician's name;
storing in a photosharing section of the memory any Digital Imaging Communications in Medicine (DICOM) formatted medical images;
storing in a filesharing section of the memory any JPEG formatted medical images;
causing display of the processed medical image and the notification; and
visually distinguishing the processed medical image in the notification from the unprocessed medical images in the queue that are yet to be processed.

13. The method of claim 12, further comprising storing the processed medical image in a database in the memory.

14. The method of claim 13, further comprising storing the processed medical image in the database in both a first format and a second format different from the first format.

15. The method of claim 14, further comprising transmitting, as part of the request, an indication of which format of the processed medical image is to be transmitted.

16. The method of claim 15, further comprising receiving the processed medical image in either the first format or the second format based on a capability of the processor.

17. The method of claim 12, wherein the processed medical image is at least one of X-ray, magnetic resonance imaging, computed tomography, electrocardiogram, ultrasonography, nuclear medicine, or radiography in digital or analog form.

18. The method of claim 12, wherein receiving the notification comprises receiving an instant message.

19. A non-transitory computer-readable storage medium containing instructions which, when executed on a computer, perform a method, the method comprising:
receiving a notification indicating that a processed medical image is available for transmission from a remote location and indicating unprocessed medical images in a queue that have yet to be processed for display;
receiving a user input to retrieve the processed medical image;
transmitting a request for the processed medical image after receipt of the notification;
receiving the processed medical image;
storing the processed medical image in memory;
creating a list of medical images stored in the memory;
indexing the list of medical images based on a patient's name and on a physician's name;
storing in a photosharing section of the memory any Digital Imaging Communications in Medicine (DICOM) formatted medical images;
storing in a filesharinq section of the memory any JPEG formatted medical images;
causing display of the processed medical image and the notification; and
visually distinguishing the processed medical image in the notification from the unprocessed medical images in the queue that are yet to be processed.

20. The non-transitory computer-readable storage medium according to claim 19, further comprising instructions for storing the processed medical image in a database in the memory.

21. The non-transitory computer-readable storage medium according to claim 19, further comprising instructions for storing the processed medical image in both a first format and a second format different from the first format.

22. The non-transitory computer-readable storage medium according to claim 21, further comprising instructions for transmitting, as part of the request, an indication of which format of the processed medical image is to be transmitted.

23. The non-transitory computer-readable storage medium according to claim 19, wherein the processed medical image is at least one of X-ray, magnetic resonance imaging, computed tomography, electrocardiogram, ultrasonography, nuclear medicine, or radiography in digital or analog form.

24. The non-transitory computer-readable storage medium according to claim 19, wherein receiving the notification comprises receiving an instant message.

* * * * *